United States Patent
Farooqi et al.

(10) Patent No.: US 6,313,073 B1
(45) Date of Patent: Nov. 6, 2001

(54) ANTI-SPROUTING AGENT FOR POTATO TUBER AND A METHOD FOR PRODUCING THE SAME

(75) Inventors: Alaul Hasan Abad Farooqi; Kishan Kumar Agarwal; Shabih Fatima; Ateeque Ahmad; Srikant Sharma; Sushil Kumar, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/538,734

(22) Filed: Mar. 30, 2000

(51) Int. Cl.⁷ .............................. A01N 31/02; A01N 35/02
(52) U.S. Cl. ............................................ 504/348; 504/353
(58) Field of Search ...................................... 504/348, 353

(56) References Cited

U.S. PATENT DOCUMENTS 5,129,951 * 7/1992 Vaughn et al. .......................... 71/122
5,139,562 * 8/1992 Vaughn et al. ............................ 71/88

* cited by examiner

*Primary Examiner*—S. Mark Clardy
(74) *Attorney, Agent, or Firm*—Shlesinger, Arkwright & Garvey LLP

(57) ABSTRACT

The invention relates to a novel antisprouting agent for tubers, said antisprouting agent comprising a mixture of essential oils obtained from aromatic plant in an amount sufficient to inhibit the growth of tubers optionally together with conventional additives and carriers.

18 Claims, No Drawings

ANTI-SPROUTING AGENT FOR POTATO TUBER AND A METHOD FOR PRODUCING THE SAME

FIELD OF THE INVENTION

The present invention relates to a novel anti-sprouting agent useful in inhibiting the growth of potato tuber. More particularly, the invention relates to identification of terpenoids (particularly acyclic aldehyde and alcohols including citronellol and citranellal and especially geraniol and citral) which may be used to inhibit tuber sprouting. In addition, the said anti-sprouting agent checks loss of fresh weight, rotting and fungal growth. These acyclic and cyclic monoterpenes exhibit substantially greater effectiveness than the compounds described in the prior art. The terpenoids may replace synthetic compounds as these are extracted from aromatic plants and they are volatile in nature.

BACKGROUND OF THE INVENTION

Potato tubers are harvested, allowed to suberize at warm temperatures for about 10 days, gradually cooled down to the storage temperature of about 10° C. For the first 1–2 months after harvest, the tubers remain dormant and exhibit little inclination to sprout. However, after this period the tubers must be chemically treated to prevent sprouting as sprouting cause numerous deleterious effects to the tubers. These include a loss of fresh weight, the conversion of starch to sugars, and a decrease in the quality and appearance of tubers. Sprouts and the surrounding tissue also contain elevated levels of toxic glycoalkaloids, which are not destroyed by cooking. Forsythe et al. suggested that sprouting of stored potatoes may be eliminated or minimized by a treatment with chlorpropham (CIPC, 1-methylethyl-3-chlorophenylcarbamate) and DMP (dimethylnaphthalene) (U.S. Pat. No. 5,965,489, 1999). CIPC is currently used to control sprouting by the industry. Although CIPC has been used effectively for over three decades, questions concerning its toxicity have been raised, and it is currently under review by the Environmental Protection Agency. CIPC is known to be among the three pesticides found in the highest concentrations in the diet of an average American [Gartrell et al. J.Assoc. Off. Anal. Chem. 69: 146–159, 1986] and comprises over 90% of the synthetic residues found in U.S. potatoes [Klocke et al., J. Chem. Ecol. 13: 2131–2141; 1987]. Therefore, a pressing need exists to find other, more environmentally acceptable sprout inhibitors for tubers. Currently, several research groups in the United States and Europe are investigating alternative chemical inhibitors Rama and Narasimham, J Food Sci Technol., 24: 40–42, 1987; Aliaga and Feldheim Ernahrung, 9: 254–256, 1985 and ; Feldheim, "Practicability and mode of action of quality storage of potatoes after harvest" in Report of the lecture given to the German Institute for quality research [Plant Nutrition Products; March 1985, 6 pages] reported that oil from the Muna plants from south America was more effective than CIPC in inhibiting sprouting, fresh weight loss, and the incidence of rotted tuber parts over a period of 120 days. The authors also reported that the main components of the oil, including the monoterpenes alpha and beta-pinene and limonene, and the oxygenated monoterpenes pulegone and menthone/isomenthone are effective in this regard. Vaughn et al. reported a method for inhibiting sprouting of tubers including the step of exposing tubers to the oxygenated monoterpenes ("Inhibition of potato sprouting using volatile monoterpenes" U.S. Pat. No. 5,139,562, 1992.).

Some plants release certain chemicals in their immediate environment, which inhibit or stimulate nearby growing plants. The phenomenon is referred to as allelopathy and such plants are known as allelopathic plants (Bagchi et al., Phytochemistry, 45: 1131–1133 1997, koitabshi et al., J. Plant Res, 110: 1–6, 1997). A variety of allelochemicals have been identified including phenolic acids, coumerins, terpenoids, flavonoids, alkaloids, glycosides etc. (Putnam and Tang (ed.), The Science of Allilopathy, John Wiley & Sons, N.Y. 1986, Rice, Allelopathy, $2^{nd}$ ed. Academic Press, New York, 1984). The chemicals are considered as resources for developing herbicides, plant growth stimulators and pharmaceuticals. The allelopathic potential of volatiles from *Echinacea angustifolia* have been examined on lettuce seeds. (Viles & Reese Environ. and Expt Botany, 366:39–43, 1996). Certain aldehydes such as citral, cinnamaldehyde, salicyladehyde, and benzaldehyde may be inhibitors of growth and germination (Steward & Krikorian, Plants, chemicals and growth, 1971 Academic Press, New York and London).

Salvia is known to produce volatile inhibitors. The air around Salvia has been reported to contain two terpenes i.e. cineole and camphor. Cineole inhibited germination and growth of *Brassica compestris* (Koitabashi et al., J. Plant Res. 110,: 1–6, 1997). The inhibitory action of volatile oil and its constituents of *Thymus capitatus* was tested on its own seed germination. Seed germination and seedling growth was inhibited (Vokou et al., Acta Oecol Plant, 7: 157–163, 1986). Extract of *Acori rhizoma* and *Acorus calamus* was shown to inhibit germination of lettuce seeds. (Nawamaki el al. 1996, Phytochem. 43: 1175–1182). Essential oil of *H. ringens* showed significant anti-germinating properties (Von Poser et al. 1996, J. Agric. & Food Chem, 44: 1829–1832). The oil of *H. ringens* is constituted mainly by pulegone. Reynolds reported comparative effects of acyclic compounds and quinones on inhibition of lettuce fruit germination (Ann. of Bot. 60: 215–223). Owen Asplund reported 'Monoterpenes: Relationship between structure and inhibition of germination (Phytochemistry 7: 1995–1997, 1968).

The allelopathic activity of the essential oils of three Nigerian medicinal plants have been examined (Oguntimen et al 1989, Planta Medica 55: 219). *Piper guineese* oil showed mild root inhibition from 25 ppm to 100 ppm. Above 100 ppm, the inhibition was significantly higher i.e. 50% at 400 ppm and 57% at 800 ppm. Effect of certain essential oils and four monoterpenoids has been examined on sprouting of stored potato tubers at room temperature. The essential oils of peppermint, ajowain, basil, spearmint and monoterpenoids such as carvone, linalool, methyl chavicol and anethol were the most effective (Singh et al. 1997, Pesticide Res J 9: 121–124). An antisprouting agent for potatoes based on the essential oil of caraway (rich in carvone) has been suggested (Capelle et al. 1997, Rev. A & M plants 3(3) no. 1452 pp 183). De Vries has reported that a combination of carvone and one or more fungicides leads to synergistic effect for inhibiting sprouting (U.S. Pat. No. 6,001,773, 1999). Benzaldehyde, salicylaldehyde and substituted benzoic acids have been found in uncooked and baked potato tubers [Coleman et al., J. Agric. Food Chem., 29: 42–49 (1981)]. These compounds have been shown to be inhibitory to the growth of plants, fungi, and bacteria. [Kurita et al. Agric. Biol. Chem. 45: 954–952, 1981].

The above described chemicals used for checking sprouting of potatoes suffer from number of disadvantages 1. Some chemicals do not show 100% inhibition of potato tubers
2. The chemicals are not easily available in the market as they are not industrially produced 3. Chemicals are costly.

4. CIPC is synthetic chemical and its residue is left in the tubers which is harmful for human body.

To overcome the drawbacks in the prior art, the applicants have developed a novel formulation useful as an anti-sprouting agent for inhibiting tuber sprouting without necrosis or softening of the tuber, especially in potatoes.

OBJECTS

The main object of the present invention is to provide a novel anti-sprouting agent for inhibiting tuber sprouting without necrosis or softening of the tuber, in potatoes.

Another object of the present invention is to provide an anti-sprouting agent for inhibiting the sprouting of tubers under storage using a cyclic monoterpene compounds, as volatiles or as emulsions.

Still another object of the present invention is to provide an anti-sprouting agent comprising terpenoids obtained from herbs, so that the agent is safe, ecofriendly easily available and does not exhibit adverse effect on potatoes and can effectively be used as antisprouting agents.

Yet another object of this invention is to provide an anti-sprouting agent for inhibiting tuber sprouting using a compound that has low mammalian toxicity, is rapidly biodegradable, is inexpensive, and which does not impart an unpleasant taste or odour to the treated tubers.

Still another object of the invention is to provide an anti-sprouting agent for inhibiting tuber sprouting which also prevents or controls fungal growth upon the tubers, thereby reducing postharvest decay losses.

SUMMARY

Accordingly, the present invention provides a novel anti-sprouting agent for inhibiting growth of potato tubers, said agent comprising acyclic monoterpene compounds obtained from a group of essential oils present in aromatic plants comprising *Cymbopogon martini, C.flexuosus, C.winterianus, Mentha arvensis, Ocimum sanctum, Mentha piperita, Artemisa annua, Eucalyotus citradora, Lavendula officinalis* and *Cederus deodara*. Further, the invention provides a novel antisprouting agent comprising acyclic monoterpenes such as citral, geraniol, citronellol, and citronellal and conventional carriers and additives. The anti-sprouting agent comparatively cheaper than cyclic monoterpenes. The invention also provides a method for the preparation of the said antisprouting agent and a method for application of the said antisprouting agent to tubers to inhibit their growth.

DETAILED DESCRIPTION

Accordingly, the invention provides novel antisprouting agent comprising essential oils/monoterpenes obtained from aromatic plants in an amount sufficient to inhibit the growth of tubers together with conventional additives and carriers.

In an embodiment, the essential oils in the antisprouting agent are obtained from a group of aromatic plants selected from *Cymbopogon martini, C.flexuosus, C.winterianus, Mentha arvensis, Ocimum sanctum, Mentha piperita, Artemisa annua, Eucalyptus citradora, Lavendula officinalis* and *Cederus deodara*.

In another embodiment, the oils in the antisprouting agent are selected from the group of monoterpenes comprising citral, geraniol, citronellol, and citronellal.

Yet another embodiment, the essential oil of the antisprouting agent is present at a concentration of 4–10 mM.

One another embodiment, the monoterpenes of the antisprouting agent are used in substantially pure form or as available in the oil.

In still another embodiment, the conventional carriers and additives used in the said antisprouting agent are selected from the group comprising water, aromatic aldehydes or alcohols, cyclic and acyclic alcohols or aldehydes and other organic solvents.

The applicants hereby state that the antisprouting agent contains essential oils/acyclic monoterpenes in an amount sufficient to inhibit the growth of tubers. Conventional carriers and additives are added in the antisprouting agent in an amount so as to enhance the activity of the essential oils. The antisprouting agent may be formulated in various physical forms such as sprays, powder, emulsion, etc. It may also be mixed with fungicides or insecticides. Therefore, the carriers or additives that may be mixed with the essential oils/acyclic monoterpenes of the antisprouting agent will vary depending upon the physical form in which the agent is formulated. The exact amount of combination of the essential oils/acyclic monoterpenes and the conventional additives may be readily determined by a person skilled in the art at the time of making the formulation. It is recommended that the formulation useful as natural antisprouting agent for potato tubers comprise citral, geraniol, citronellol or a combination in equal proportion at a concentration of 4–8 mM wherein the tubers may be dipped in solution, sprayed or exposed to vapours of the compounds.

In a preferred embodiment, exposure of the tubers to the aromatic acyclic alcohols or aldehydes involve exposure of the subject compounds while in liquid form, such as by dipping or spraying with a solution or emulsion thereof Suitable formulations of the aromatic aldehydes or alcohols may include a variety of well known solvents or suspending agents, including, but not limited to water. It is also understood that emulsifying agents may also be used. Alternatively, the tubers may be exposed to the aromatic alcohols or aldehydes involving exposure to the subject compounds while in a vapor phase. This method takes advantage of the relatively high volatility of these compounds, and enjoy the benefit of ease of application over a large volume of tubers.

In an embodiment of the invention the acyclic monoterpene compounds may be synthetic or naturally occurring and not limited to oils such as palmarosa oil (containing geraniol), lemongrass oil (containing citral).

In another embodiment of the invention the acyclic monoterpenes (citral, geraniol, citronellol, citronellal etc.) may be formulated with solvents or inert carriers like water.

In yet other embodiment of the invention, wherein the acylic monoterpenes may be further formulated with other emulsifying agents and fungicide or insecticides.

In yet another embodiment of the invention the formulation is effective for the inhibition of sprouting of tubers but not limited to potatoes.

The monoterpenes used in this invention were obtained from aromatic plants. The aromatic plants yield essential oil which are composed of different types of monoterpenes. The essential oils were obtained from leaves, flowers or roots of aromatic plants by steam distillation. The plants used in this study are:

1. *Cymbopogon martini* which has high content of geraniol, geranyl acetate
2. *C.flexuosus* with high content of citral
3. *C.winterianus* rich in citronellal and citronellol 4. *Mentha arvensis* with high content of menthol and menthone
5. *Ocimum sanctum* rich in ketone, camphor
6. *Mentha piperita* has high content of menthone and menthol
7. *Artemisa annua* rich in ketone camphor
8. *Eucalyptus citradora* rich in cineole
9. *Lavendula officinalis* rich in linalool
10. *Cederus deodara* with high content of chavicol The isolated terpenoids were used as such for checking the sprouting or were further purified by TLC etc. and the purified fractions were tested for the response.

Exposure of the tubers to the composition may be initiated at any time after harvest or during the storage of the tuber. However, exposure after 1–3 month of harvest or at such time that the tubers begin to sprout should be preferred.

In the preferred embodiment the tubers may be continuously or intermittently, or only once exposed to the aldehydes and alcohols throughout the storage. Throughout the period of exposure, the tubers will exhibit resistance to sprouting. Following removal of the tubers from exposure, resistance to sprouting may diminish, tubers may begin to sprout normally in a few days, or it may be prolonged. The duration of this resistance will vary with the specific aldehyde or alcohol used, its concentration, and the length of exposure. It has been found that tubers exposed over relatively longer periods of time and/or at higher concentrations of the subject compounds may resist sprouting in definitely when removed exposure.

The absolute amount of the aromatic aldehydes or alcohols of the invention (geraniol, citral, citronellal, citronellol, menthyl acetate) and their concentration in vapour phase or liquid composition may vary and are selected to provide an effective inhibition of tuber sprouting. An effective amount is defined here in as that quantity of the compounds that significantly inhibit tuber sprouting in comparison with untreated tubers. Effective amounts include but are not limited to those quantities of the subject compounds providing approximately complete inhibition of tuber sprouting (less than about 1% of eyes sprouting during treatment with the compounds). The actual effective amount of the subject compound may vary with the specific compound used, the mode of application, the length of exposure to the compounds, the volume of the tubers to be treated, environmental conditions such as temperature, humidity and air flow (affecting volatility and tuber metabolic activity). The amount may also vary in accordance with the duration of the resistance of the tubers to sprouting following exposure that is desired.

The invention is further illustrated in detail with reference to the following examples, which are provided as illustrations of the embodiments of the invention and should not be construed as limitations on the inventive concept. Various modifications that may be apparent to one skilled in the art are deemed to fall within the scope of the invention.

EXAMPLE 1

The object of the first example was to screen volatile essential oils for sprouting inhibition. Six Potato tubers of cultivar "Pahadi Aloo" of almost equal size were kept in polythene bags or in jars with 500 mg essential oil in the beaker. The essential oil were obtained from the plants by hydrodistillation. There were three replications for each treatment and control (without essential oil ). The amount was sufficient to theoretically produce a saturated atmosphere in the bags or flasks.

The experimental results from tubers continuously exposed to essential oil for 7 days are shown in Table 1. After this period of time, control tubers had sprouted heavily. Lemongrass oil inhibited sprouting. All of the tubers in these treatments were firm and appeared healthy. Artemisia annua oil and eucalyptus oil had no significant effect on tuber sprouting inhibition while Basil oil, Japanese mint oil and peppermint oil only slightly suppressed sprouting. Sprouting inhibition was maximum with Lemongrass oil (53% )while in untreated tubers it was 17%.

TABLE 1

Sprout inhibition in potato tubers exposed to aromatic essential oils for 7 days

| Treatment | Size of potato (cm) | no. of buds | % of eyes-sprouted |
|---|---|---|---|
| Peppermint oil | 5.3 | 9.7 | 68 |
| Japanese mint oil | 5.3 | 8.3 | 66 |
| Basil oil | 7.3 | 9.3 | 74 |
| Artemisia oil | 6.0 | 9.3 | 80 |
| Eucalyptus oil | 6.0 | 9.3 | 80 |
| Lemongrass oil | 6.0 | 8.0 | 54 |
| Control | 7.0 | 11.3 | 81 |
| LSD (5%) | 1.9 | 2.7 | 34 |

EXAMPLE 2

The object of the second example was to screen some more essential oils for sprout inhibition which could not be taken up in the first example. Potato tubers of cultivar "Pahadi aloo" were purchased from the market which has been stored at 4° C. for 3–5 months after harvest. Tubers were kept in 30 cm transparent polythene bags for checking the sprouting. Five potato tubers of almost equal size were kept in bags with 500 mg of liquid essential oil in 10 ml beaker. There were three replications for each treatment and three replications for control (without essential oil). The sample bags were then stappled. Tubers were kept at ambient temperature for 7 days, at which time all control tubers displayed sprouting. The experimental results from tubers continuously exposed to essential oils for seven days are shown table 2. After this period of time, control tubers had sprouted heavily. Citronella oil, palmarosa oil and lemongrass oil significantly inhibited sprouting and inhibition was 32–37% while in control tubers, it was 15%. Lavender oil and cedarwood oil had no significant effect on tuber sprouting.

TABLE 2

| Treatment | Size of tuber (cm) | No. of buds | % of sprouted buds |
|---|---|---|---|
| Lavender oil | 9.0 | 11.0 | 81.0 |
| Citronella oil | 7.0 | 11.0 | 60.0 |
| Palmarosa oil | 6.3 | 9.3 | 60.0 |
| Lemongrass oil | 5.3 | 10.0 | 63.0 |
| Mosquito-repellent | 8.0 | 12.0 | 69.0 |
| Cedarwood oil | 6.3 | 11.0 | 84.0 |
| Control | 8.0 | 13.3 | 85.0 |
| LSD (5%) | 1.8 | 1.7 | 17.9 |

EXAMPLE 3

Tubers treated with essential oils did not show complete inhibition of sprouting, although significant inhibition was observed. Therefore essential oils were purified by column chromatography and substantially pure compounds were used.

Emulsion of the compounds were prepared of 8 mM concentration of each compound in distilled water containing $2 \times 10 - 6\%$ Tween 20 as emulsifier (control tubers were treated with Tween 20 only). Tubers were treated by dipping each tuber in emulsion for 5 hours, where upon excess liquid was allowed to drain off. Six tubers per treatment were used, with two replicates, and all experiments were repeated once. Tubers were then kept in jars for 10 days at ambient temperature. Tubers were then evaluated as in example 1 & 2 for percentage of sprouted eyes, tuber texture and fungal growth.

Results are shown in Table 3 All control tubers displayed heavy sprouting after 10 days. Only geraniol, and citral completely inhibited sprouting and no rotting was observed. Geranyl acetate inhibited sprouting by 42%. Camphor, linalool, 1-carvone and d-carvone and a combination of linalyl acetate and 1-carvone had no significant effect on tuber sprouting. It is of interest to note that 1-carvone and d-carvone displayed little or no inhibition of sprouting even though this compound has been reported to inhibit sprouting in potatoes [Capelle et al. 1997, Rev. A&M plants 3 (3) no. 1452 pp 183].

Geraniol and citral emulsions completely inhibited sprouting when tubers were treated again for 5 hours and kept for 10 days and then again dipped for treatment. In this way tubers remained completely dormant even after two months. Geraniol, citral, citranellol, citranellal and menthyl acetate were as effective as reported monoterpenes such as benzaldehyde, cinnamaldehyde, eugenol and thymol (U.S. Pat. No. 5,129,951).

TABLE 3

| Treatment | size | % eyes sprouted |
|---|---|---|
| Control | 5.3 | 100 |
| Geranyl acetate | 6.6 | 58 |
| Geraniol | 6.2 | 16 |
| Camphor | 6.0 | 89 |
| Citral | 6.7 | 19 |
| Linalool | 6.1 | 100 |
| l-carvone | 6.2 | 100 |
| d-carvone | 5.8 | 93 |
| d-citronellol | 5.8 | 17 |
| l-citronellol | 5.1 | 0.0 |

EXAMPLE 4

Tubers were treated with geraniol and citral the two promising chemicals at different concentrations. The terpenes were applied at 4 mM, 6 mM and 8 mM for 5 hours by dipping the tubers and then the tubers were kept in jars for 12 days. Sprouting was completely inhibited at 6 and 8 mM concentrations. The experiment was continued till 20 days after treatment and sprouting was not observed. The results are given in table 4

TABLE 4

| Treatment | concentration | Size of potato | % eyes sprouted |
|---|---|---|---|
| Geraniol | 4 mM | 5.3 | 7.5 |
| | 6 mM | 4.7 | 0.0 |
| | 8 mM | 5.7 | 0.0 |
| Citral | 4 mM | 5.4 | 4.1 |
| | 6 mM | 5.0 | 0.0 |
| | 8 mM | 5.2 | 0.0 |
| Control | — | 5.5 | 100.0 |

EXAMPLE 5

Combination of 4–8 mM of each geraniol, citral, citronellol and citronellal were tried to determine the best combination. Along with this some other compounds were also tried. The terpenes were applied by dipping the tubers for five hours in aqueous solution of the monoterpenes containing Tween 20 as emulsifying agent. A combination of citral, citronellol and geraniol in pairs as well as altogether in a concentration ranging between 6–8 mM was most effective and complete inhibition in sprouting was observed even after 14 days. Other chemicals were not very effective. Results are given in table 5. Menthol, anisaldehyde, thymol, cinnamom bark oil and thymol has been used earlier (U.S. Pat. No. 5,129,951) and were effective.

TABLE 5

| Treatment | size of potato | % eyes sprouted After 3 days | after 7 days | after 14 days |
|---|---|---|---|---|
| Geraniol + citral | 5.7 | 0.0 | 0.0 | 0.0 |
| l-citronellol + geraniol | 5.8 | 0.0 | 0.0 | 0.0 |
| citronellol + citral | 5.6 | 0.0 | 0.0 | 0.0 |
| Citonellol + geraniol + citral | 5.4 | 0.0 | 0.0 | 0.0 |
| Menthyl acetate | 6.0 | 0.0 | 0.0 | 0.0 |
| Menthol | 5.8 | 29 | 29 | 29 |
| Anisaldehyde | 5.7 | 78 | 96 | 96 |
| Cinnamom bark oil | 5.3 | 0.0 | 14 | 50 |
| Thymol | 5.8 | 79 | 98 | 98 |
| Anethol | 5.7 | 0.0 | 0.0 | 51 |
| Control | 6.0 | 100 | 100 | 100 |

EXAMPLE 6

Tubers treated with emulsions of different aromatic compounds remained dormant. Therefore, it was tried to find out the response when tubers were exposed to vapours of volatilized compounds for sprout inhibition. Substantially pure compounds were used as in other examples. Six potatoes were placed in air tight jars containing 9 cm piece of filter paper saturated with one ml of the liquid compound. These amounts were sufficient to produce a saturated atmosphere in the flask. The filter paper was placed in the cap of the flask so that no direct physical contact with the tuber occurred. The tubers were removed after seven days and placed in flasks containing fresh air at ambient temperature. Control tubers were placed in sealed flask lacking any added compound. The results fourteen days after removal of the tubers from exposure to vapours of geraniol, citral, citronellol, citronellal and menthyl acetate are shown in table 6. Control tubers displayed complete sprouting after 14 days. Citral, geraniol, citronellol, citronell, and menthyl acetate completely inhibited sprouting and tubers remained unsprouted 18 days after the tubers were removed from treatment flask. Most treated tubers also remained firm to the touch and lacked any visible rotting or fungal growth after this time period. The observations herein above suggest that tubers may only need treatment for a relatively short period of time and that continual application would not be necessary for long term storage. Such short term treatment would greatly lessen costs to the potato industry.

TABLE 6

Tubers sprouting 14 days after exposure to volatized aromatics for seven days.

| Treatment | size of potatoes | % eyes sprouted |
|---|---|---|
| Control | 6.0 | 100 |
| Geraniol | 6.1 | 0.0 |

TABLE 6-continued

Tubers sprouting 14 days after exposure to volatized aromatics for seven days.

| Treatment | size of potatoes | % eyes sprouted |
| --- | --- | --- |
| Citral | 5.5 | 0.0 |
| d-Citronellol | 6.3 | 0.0 |
| citronellal | 5.9 | 0.0 |
| menthyl acetate | 6.2 | 0.0 |

EXAMPLE 7

The tubers were exposed to fumes of citral with the help of a vaporizer at ambient temperature in a close atmosphere for 24 hour, 48 hour and 96 hours. The tubers were then placed in flask containing fresh air and free of any additional volatilized compound. Control tubers were placed in sealed flasks lacking any added compounds. Fourteen days after treatment all tubers examined for percentage of eyes sprouted, tuber texture and fungal growth. The results are shown in the table 7

Table no. 7 Tuber sprouting 14 days after exposure to volatilized aromatics for 1, 2, or 4 days

TABLE 7

Tuber sprouting 14 days after exposure to volatilized aromatics for 1, 2, or 4 days

| Treatment | size oftubers | % eyes sprouted |
| --- | --- | --- |
| Control | 6.1 | 100 |
| 1 Day | 6.0 | 18.5 |
| 2 Days | 6.2 | 8.3 |
| 4 Days | 5.6 | 0.0 |

Adavantages

1. The anti-spouting agent is safe for use and the components used in the agent are of herbal origin and do not produce any adverse effect on the potatoes.

2. The anti-spouting agent is ecofriendly and economically viable.

3. No harmful components are used which ultimately spoil the potatoes.

What is claimed is:

1. A novel antisprouting agent for tubers, said antisprouting agent comprising a mixture of acyclic monoterpene compounds, said acyclic monoterpene compounds selected from the group consisting of citral, geraniol, citronellol and citronellal derived from essential oils of aromatic plants, said mixture of acyclic monoterpene compounds provided in an amount sufficient to inhibit the growth of tubers.

2. An anti-sprouting agent as claimed in claim 1 wherein said essential oils are obtained from a group of aromatic plants comprising *Cymbopogon martini, C. flexuosus, C. winterianus, Mentha arvensis, Ocimum sanctum, Mentha piperita, Artemisia annua, Eucalyptus citadora, Lavendula officinalis* and *Cederus deodara*.

3. An antisprouting agent as claimed in claim 1 wherein said compounds derived from essential oils are present at a concentration of 4–10 mM.

4. An antisprouting agent as claimed in claim 1 wherein said monoterpene compounds are at least one of in a substantially purified form or in a form as available in said essential oil.

5. An antisprouting agent as claimed in claim 1 and further including conventional additives and carriers selected from the group consisting of water, aromatic aldehydes, aromatic alcohols, cyclic and acyclic alcohols and cyclic and acyclic aldehydes.

6. An anti-sprouting agent as claimed in claim 1 wherein said mixture of acyclic monoterpene compounds comprises citral, geraniol, citronellol, and citronellal in equal proportions and at a concentration of 4–8 mM.

7. An anti-sprouting agent as claimed in claim 1 and wherein said citral and said geraniol are derived from lemongrass oil and palmarosa oil respectively.

8. An anti-sprouting agent as claimed in claim 1 wherein said mixture of cyclic monoterpene compounds further includes at least one fungicides or insecticides.

9. A method for promoting anti-sprouting in tuber plants, the method comprising the steps of:

a) providing a mixture of acyclic monoterpene compounds, the acyclic monoterpene compounds selected from the group consisting of citral, geraniol, citronellol and citronellal derived from essential oils of aromatic plants; and b) applying the mixture to a tuber plant, the mixture in an effective amount sufficient to promote antisprouting in the tuber plant.

10. The method of claim 9 and further including the step of:

a) combining the mixture with an effective amount of at least one of carriers, additives and solvents.

11. The method of claim 9 and wherein:

a) the essential oils are obtained from a group of aromatic plants comprising *Cymbopogon martini, C. flexuosus, C. winterianus, Mentha arvensis, Ocimum sanctum, Mentha piperita, Artemisia annua, Eucalyptus citadora, Lavendula officinalis* and *Cederus deodara*.

12. The method of claim 10 and wherein:

a) the at least one of carriers, additives and solvents are selected from the group comprising water, aromatic aldehydes or alcohols, cyclic and acyclic alcohols or aldehydes.

13. The method of claim 9 and wherein:

a) the mixture of acyclic monoterpene compounds are present at a concentration of about 4–10 mM.

14. The method of claim 9 and wherein:

a) the mixture is applied to the tuber plant by at least one of dipping the tuber in a solution of the mixture, spraying the tuber plant with the mixture and exposing the tuber plant to vapours of the mixture.

15. The method of claim 9 and wherein:

a) the citral and the geraniol are derived from lemongrass oil and palmarosa oil respectively.

16. The method of claim 9 and wherein:

a) the mixture comprises citral, geraniol, citronellol, citronellal or a combination thereof in equal proportion at a concentration of 4–8 mM.

17. The method as claimed in claim 9 and wherein:

a) the mixture further includes at least one of emulsifying agents, fungicides and insecticides.

18. The method as claimed in claim 9 and wherein:

a) the tuber plant is a potato.

\* \* \* \* \*